(12) United States Patent
Liess et al.

(10) Patent No.: US 8,441,368 B2
(45) Date of Patent: May 14, 2013

(54) RADIATION GUIDE FOR A DETECTOR, SCATTERED RADIATION DETECTOR

(75) Inventors: Martin Liess, Hochheim Am Main (DE); Arthur Barlow, Alton (GB)

(73) Assignee: Excelitas Technologies Singapore Pte. Ltd., Solaris (SG)

( * ) Notice: Subject to any disclaimer, the term of this patent is extended or adjusted under 35 U.S.C. 154(b) by 417 days.

(21) Appl. No.: 12/678,865

(22) PCT Filed: Sep. 19, 2008

(86) PCT No.: PCT/EP2008/007898
§ 371 (c)(1),
(2), (4) Date: Jul. 22, 2010

(87) PCT Pub. No.: WO2009/036988
PCT Pub. Date: Mar. 26, 2009

(65) Prior Publication Data
US 2010/0309013 A1    Dec. 9, 2010

(30) Foreign Application Priority Data
Sep. 20, 2007   (DE) .......................... 10 2007 045 018

(51) Int. Cl.
*G08B 23/00* (2006.01)
*G01J 1/00* (2006.01)
*G02B 5/00* (2006.01)

(52) U.S. Cl.
USPC ........ 340/693.6; 340/600; 340/619; 340/628; 340/629; 340/630; 250/336.1; 250/339.11; 250/347; 250/353; 250/227.14; 250/505.1; 359/833

(58) Field of Classification Search ............... 340/693.6, 340/628, 629, 630
See application file for complete search history.

(56) References Cited

U.S. PATENT DOCUMENTS

| | | | |
|---|---|---|---|
| 5,451,931 A * | 9/1995 | Muller et al. | 340/630 |
| 5,821,866 A | 10/1998 | Bernal et al. | |
| 6,107,925 A | 8/2000 | Wong | |
| 6,560,038 B1 * | 5/2003 | Parkyn et al. | 359/726 |
| 6,756,906 B2 | 6/2004 | Bernal et al. | |
| 6,778,091 B2 | 8/2004 | Qualey, III et al. | |
| 2001/0038338 A1 | 11/2001 | Kadwell et al. | |

FOREIGN PATENT DOCUMENTS

| | | |
|---|---|---|
| DE | 198 21 335 A1 | 11/1999 |
| DE | 100 12 613 A1 | 10/2001 |
| EP | 0 571 077 A2 | 11/1993 |
| EP | 0 588 232 B1 | 7/1997 |
| EP | 1 087 221 A1 | 3/2001 |
| EP | 1 112 716 A1 | 7/2001 |
| GB | 2314618 A | 1/1998 |
| GB | 2330410 A | 4/1999 |
| GB | 2 342 987 A | 4/2000 |
| GB | 2 389 176 A | 12/2003 |

(Continued)

*Primary Examiner* — Donnie Crosland
(74) *Attorney, Agent, or Firm* — Peter A. Nieves; Sheehan Phinney; Bass + Green PA

(57) ABSTRACT

A surface mountable radiation guide for a radiation path between a measurement volume (1) and an electro-optical component has a first radiation interface in a radiation path towards the measurement volume, a third radiation interface in a radiation path towards the electro-optical component, and a reflecting portion forming a first radiation path between the first and the third radiation interface, said first radiation path providing a focus region at the measurement volume.

36 Claims, 4 Drawing Sheets

FOREIGN PATENT DOCUMENTS

| | | |
|---|---|---|
| JP | 56-022936 | 3/1981 |
| JP | 56-022937 | 3/1981 |
| JP | 04-160696 | 6/1992 |
| JP | 2003-098083 | 4/2003 |
| WO | 2004104959 A | 12/2004 |

* cited by examiner

RADIATION GUIDE FOR A DETECTOR, SCATTERED RADIATION DETECTOR

BACKGROUND

1. Field

The aspects of the disclosed embodiments relate to a radiation guide for a radiation detector, and a scattered radiation detector.

2. Brief Description of Related Developments

Scattered light detectors may for example be smoke detectors. Such detectors comprise a radiation source, for example an LED (light emitting diode), and a radiation sensor sensitive for the emitted radiation. The two components are in one embodiment arranged such that the sensor is prevented from receiving direct radiation from the source. Rather, radiation received by the sensor would be radiation scattered by particles, for example smoke particles, in the ambient atmosphere. The disadvantage of the known scattered light sensors is that either sensitivity is poor because both on the side of the radiation emitting device and on the side of the sensing device the numerical aperture is small so that the signal is weak, or if a large aperture is desired, the device becomes voluminous.

Another disadvantage is that light from the optical emitter scattered from parts of the smoke detector itself can be received by the detector and leads to an offset that might vary due to surface contamination and ageing. Such variable offset increased the detection threshold for smoke to be detected.

Another technology for detecting smoke in the atmosphere (or generally: scattering particles in an ambient fluid) is to establish a direct line of sight between a radiation source and a sensor (which may also include mirrors), and using the effect that scattered-out intensity reduces the signal sensed by the sensor. In these sensors, the detection signal is weaker than the non-detection signal. For increasing sensitivity, a long optical path is desired for achieving a larger accumulated intensity-weakening effect by a given particle concentration. Such optical paths may be lengthened by providing folded paths, e.g. a pentagram-like path using mirrors. This again leads to a comparatively bulky device.

Known prior art documents for the addressed technology are U.S. Pat. Nos. 6,778,091 B2, 6,756,906 B2, GB 2 389 176 A, U.S. 2001/0038338 A1, U.S. Pat. No. 6,107,925, GB 2 342 987 A, U.S. Pat. No. 5,821,866, GB 2 314 618 A and EP 0 588 232 B1.

SUMMARY

It is the object of the disclosed embodiments to provide a radiation guide allowing the construction of a small sized scattered light detector of sufficient sensitivity, while providing a low offset from light that is scattered from parts other than the smoke to be detected.

This object is accomplished in accordance with the features of the independent claims. Dependent claims are directed on preferred aspects of the disclosed embodiments.

A surface mountable radiation guide for a radiation path between a measurement volume and an electro optical component comprises a first radiation interface in a radiation path towards the measurement volume, a third radiation interface in a radiation path towards the electro-optical component, and a reflecting portion forming a first radiation path between the first and the third radiation interface, said first radiation path providing a focus region at said measurement volume.

The radiation guide may be a massive body and of transparent material. The combination of being surface mountable and providing through a reflecting surface a focus at a measurement volume renders at the same time a large numerical aperture and a nevertheless comparatively small overall construction. The radiation guide may in the same time serve as protection for the electro-optical element and its bond wires.

In a preferred embodiment, a second radiation interface may be provided receiving directly light from the third radiation interface and rendering a second radiation path towards the measurement volume, wherein also the second radiation path provides a focus region at said measurement volume.

The third radiation interface forming the second radiation path can be used for capturing light that cannot be captured by the first radiation path, and bringing it towards the measurement volume. This again increases the aperture more than increasing the size of the device.

Two such radiation guides may be provided with the measurement volume being a common focus region of both of them. One of the radiation guides is allocated to a radiation source, the other to a radiation sensor. They may be arranged such that no direct radiation (this including reflected radiation) will reach from the radiation source to the radiation sensor.

Another radiation guide for a radiation path between a measurement volume and an electro optical component comprises a first reflector having a concave reflecting surface being a part of a rotational ellipsoid. The reflector is adapted for mounting it in relation to the electro-optical component such that a first focus region of the reflecting surface is at the electro-optical component. The second focus region of the part of the rotational ellipsoid reflecting shape may define the measurement volume or measurement region. Two such radiation guides may be formed as one common part and may again be arranged such that the one of them does not directly receive light from the other of them.

A scattered radiation detector may comprise two concave reflectors as mentioned above with the measurement volume as common focus of both shapes, whereas in the respective other focus the radiation source and the radiation sensor are mounted, respectively.

Also the parabolic reflector embodiment may be surface mountable in a way that the reflector or at least a part of it is mountable on a surface which also carries other electric components, such as the electro-optical components. But likewise, parts or all of the concave reflector portions may be formed by concave housing portions.

The radiation guides may be formed such that their respective focuses are as ideal as possible. But likewise, they may be shaped such that the focus is non-ideal in a defined manner, particularly at the measurement volume, such that the radiation convergence region is defined area or volume in order to expose said defined area or volume with radiation, or to collect radiation therefrom.

BRIEF DESCRIPTION OF THE DRAWINGS

In the following, aspects of the disclosed embodiments will be described with reference to the attached drawings in which.

DETAILED DESCRIPTION OF THE DISCLOSED EMBODIMENTS

Figure 1:
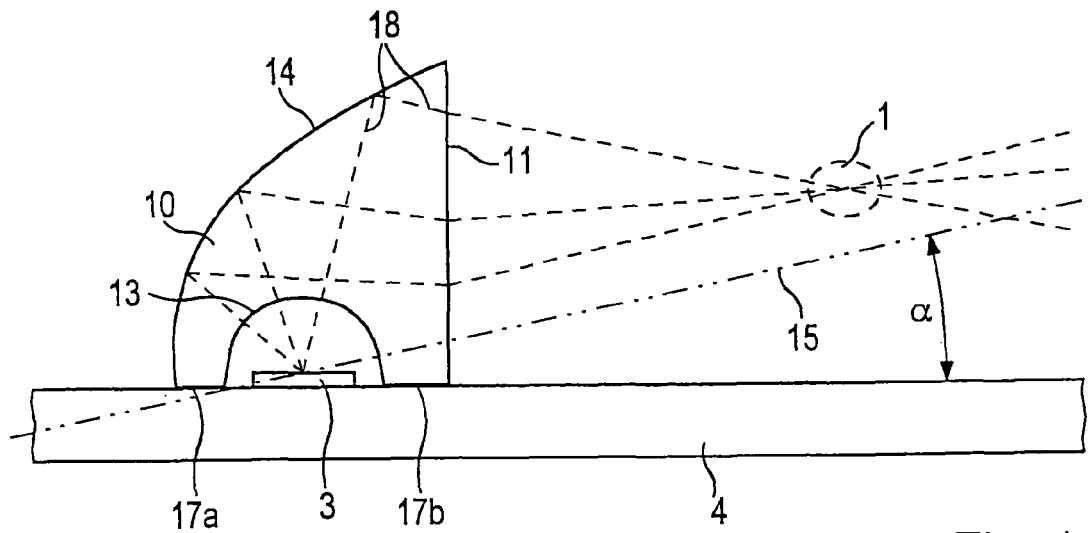
FIG. 1 shows a first embodiment of a radiation guide mounted on a surface.

Generally speaking, same reference numerals in this specification describe the same features. Features described in this specification shall be considered combinable with each other as far as not explicitly said otherwise and as far as not technically excluding each other for technological reasons.

FIG. 1 is a sectional view of a radiation guide 10. It is surface mountable in that it may be directly mounted with foot portions 17a, 17b on a mounted surface 4, for example a circuit board on which an electro-optical component 3 is mounted as well. The radiation guide comprises a first radiation interface 11 towards a measurement volume 1 and a third radiation interface 13 towards an electro-optical component 3 which may be a radiation source, for example an LED or LED chip (unpacked), or which may be a sensor or sensor chip, e.g. an infrared sensor. 14 is a reflecting surface. Reference numeral 18 denotes a first optical path extending between first interface 11 and third interface 13 and utilizing reflecting surface 14.

The radiation guide 10 may be a massive body of transparent material. The material may be resin or some kind of glass or other moldable substance. The reflecting surface 14 may be coated from outside with a reflecting substance, or may be untreated. Reflectivity may then only be given by the total or partial reflectivity at the boarder surface in dependence of the incidence angle of the light and material properties. The third interface 13, the reflecting surface 14 and first interface 11 are all together formed such that they render a first focus region or convergence region at the measurement volume 1 and a second focus region at the electro-optical component 3 or its active portion.

15 designates the optical axis defined by the geometrical shape of the reflecting surface 14. In particular embodiments, the surface 14 may be part of a rotational ellipsoid or a rotational paraboloid with the axis 15 as symmetry/rotation axis. Then, the sectional shape of the reflecting surface 14 with any of the planes including the optical axis will be a part of an ellipsis or a parabola. Depending on the shape and positioning of the first interface 11, the focus region and measurement volume 1 may be on the optical axis 15 or above or below it. FIG. 1 shows an embodiment where the measurement volume 1 is above the optical axis 15 of the reflecting surface 14, whereas in FIG. 2 the measurement volume is below the optical axis 15. The optical axis will in many embodiments reach through the effective portion of the respective electro-optical element which may sit, as far as definable for the reflecting surface 14, in (one of) its focus regions.

The first optical interface may be of flat/plain shape. Depending on its inclination angle with respect to the optical axis it bends the optical path such that the focus region and measurement volume 1 is above or right onto or below the optical axis 15. But the optical interface may generally be shaped such that a focus region appears at the measurement volume. The reflecting surface 14 may be that of a rotation paraboloid or ellipsoid. The third interface 13 may keep a distance to the electro-optical component 3. But vice versa, it may also be immediately molded onto it and possibly onto the mounting surface 4 so that the distance between the third radiation interface of radiation guide 10 and the electro-optical component 3 is practically zero. If a distance is kept between the electro-optical component 3 and the third interface 13, then said third interface surface 13 may have a concave shape. In order to support focusing of the optical beam it might have a partially or locally convex shape. In the case the electro-optical component has a very inhomogeneous reception or emission characteristics, such as most LED chips, it might have a special surface form or structure in order to compensate or make smaller such. direction-dependent inhomogeneities. It may also be a sphere-like shape with the active region of the electro-optical component 3 as center. The angle a of the optical axis 15 against the mounting surface 4 may be between 0° and 50°.

The radiation guide as shown in FIG. 1 allows a comparatively large numerical aperture or opening angle of the radiation effective at the measurement volume 1 so that at the same time a sufficient amount of effective radiation with nevertheless small construction size is obtained.

Figure 2:
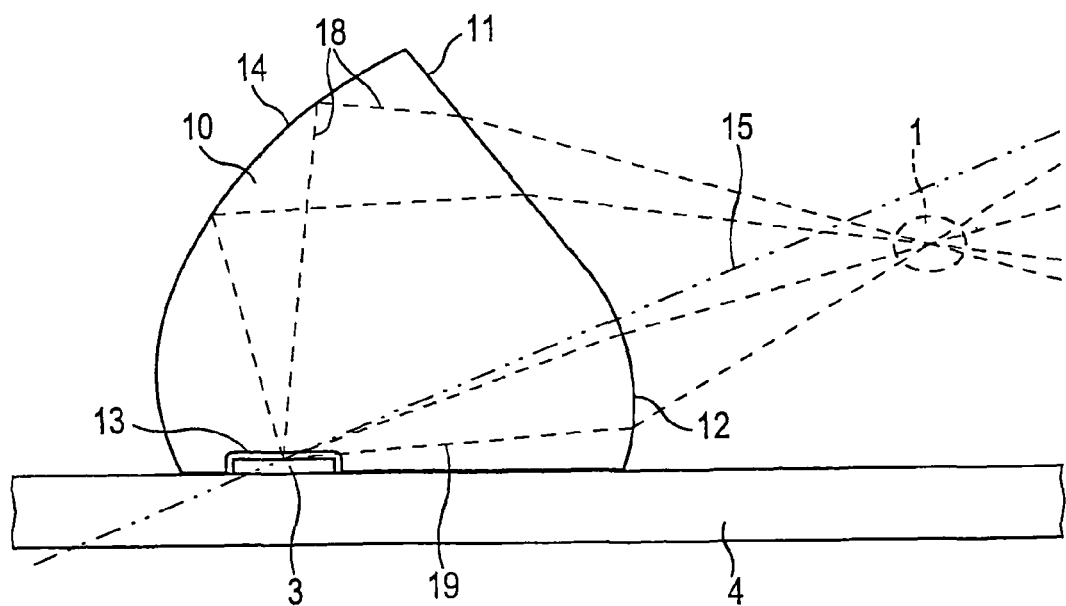
FIG. 2 shows a second embodiment of a radiation guide mounted on a surface.

FIG. 2 shows a further aspect of the disclosed embodiments. In FIG. 2, the construction of first interface 11, reflecting surface 14 and third interface 13 may be amongst each other made in the same manner as described with reference to FIG. 1. The angle a of optical axis 15 may be larger. It may for example be between 20° and 60°. The embodiment of FIG. 2 comprises a second radiation interface 12 directed towards the measurement volume 1. It receives radiation directly from the third interface 13, i.e. without a reflecting surface in between. Thus, a second radiation path 19 is formed in the radiation guide 10 that is functionally in parallel to the first radiation path 18 employing first interface 11, reflecting surface 14 and third interface 13. The second radiation interface 12 and the third radiation interface 13 may be shaped such that they focus radiation between an active area of the electro-optical component 3 and the measurement volume 1. The second radiation interface 12 may be shaped as a part of a spherical lens. Such a lens has an own optical axis independent of the optical axis of the reflecting surface 14 which is, however, not shown in the figures. The formed part of the lens may be such that it does not include the lens part through which the lenses optical axis goes.

Through this construction, the numerical aperture seen from the measurement volume 1 is again larger namely by the angular range covered by the second radiation interface 12. More radiation intensity is thus conveyed between measurement volume 1 and electro-optical component 3 so that without a substantial increase in construction size sensitivity is enhanced. Since the aperture is larger, selectivity with respect to the measurement volume is better.

FIG. 2 shows an embodiment where the measurement volume is below the optical axis 15 of the reflecting surface 14. Generally speaking, the construction should be such that the measurement volume 1 is not further away from the mounting surface 4 than any part of radiation guide 10 is away from the mounting surface 4.

The first radiation interface 11 may be or may have parts above the optical axis 15. The second radiation interface 12 may be or have parts below the optical axis 15. The transision part between first interface 11 and second interface 12 may be smooth or may be an edge or even a step in the surface depending on the required optical construction.

In FIG. 2, the radiation guide 10 is shown to be in direct contact with the electro-optical component 3 (sensor or radiation source). It may be molded onto it and its surrounding. Then, the third interface 13 does not exist as freely accessible surface and practically coincides with the surface of the active region of the electro-optical component 3.

Generally speaking, the radiation guide 10 may be prefabricated and thereafter be mounted into the mounting position through appropriate means. Mounting may for example be made by adhering it onto the substrate surface or by clamping it into an appropriate receptacle. But likewise, the radiation guide 10 may be molded onto the electro-optical element in situ. For this, the substrate/circuit board may comprise one or more alignment structures for properly positioning a mold for the radiation guide in relation to an electro-optical component.

The radiation guide may directly or indirectly be attached, molded or cast onto an electro-optical element, particularly an emitter or detector, which itself might be mounted on a substrate providing electrical terminals that allow connecting the electro-optical component to the outside and/or onto a circuit board or support with defined alignment means and possibly holding means wherein the holding means may engage with the substrate on which the electro-optical element and the radiation guide are formed.

A substrate for an electro-optical component having alignment means for a mold for a radiation guide as described in this specification is also part of the disclosed embodiments. Similarly, a substrate comprising an arrangement portion for an electro-optical component and an arrangement portion for a radiation guide as described is also part of the disclosed embodiments, the arrangement portion including preferably alignment means for said radiation guide. The alignment means may be one or more recesses and/or protrusions adapted to engage with corresponding protrusions and/or recesses at the (prefabricated) radiation guide 10 or mold thereof. The substrate may be the substrate of an entire smoke detector, or may only bear parts thereof, such as the electro-optical component, radiation guide, and contacts, and be mountable to another larger structure.

Further, the aspects of the disclosed embodiments also encompass a smoke detector component comprising a radiation guide as described in this specification, and an electro-optical element. The component may also comprise a substrate, preferably formed as described above.

Figure 3:
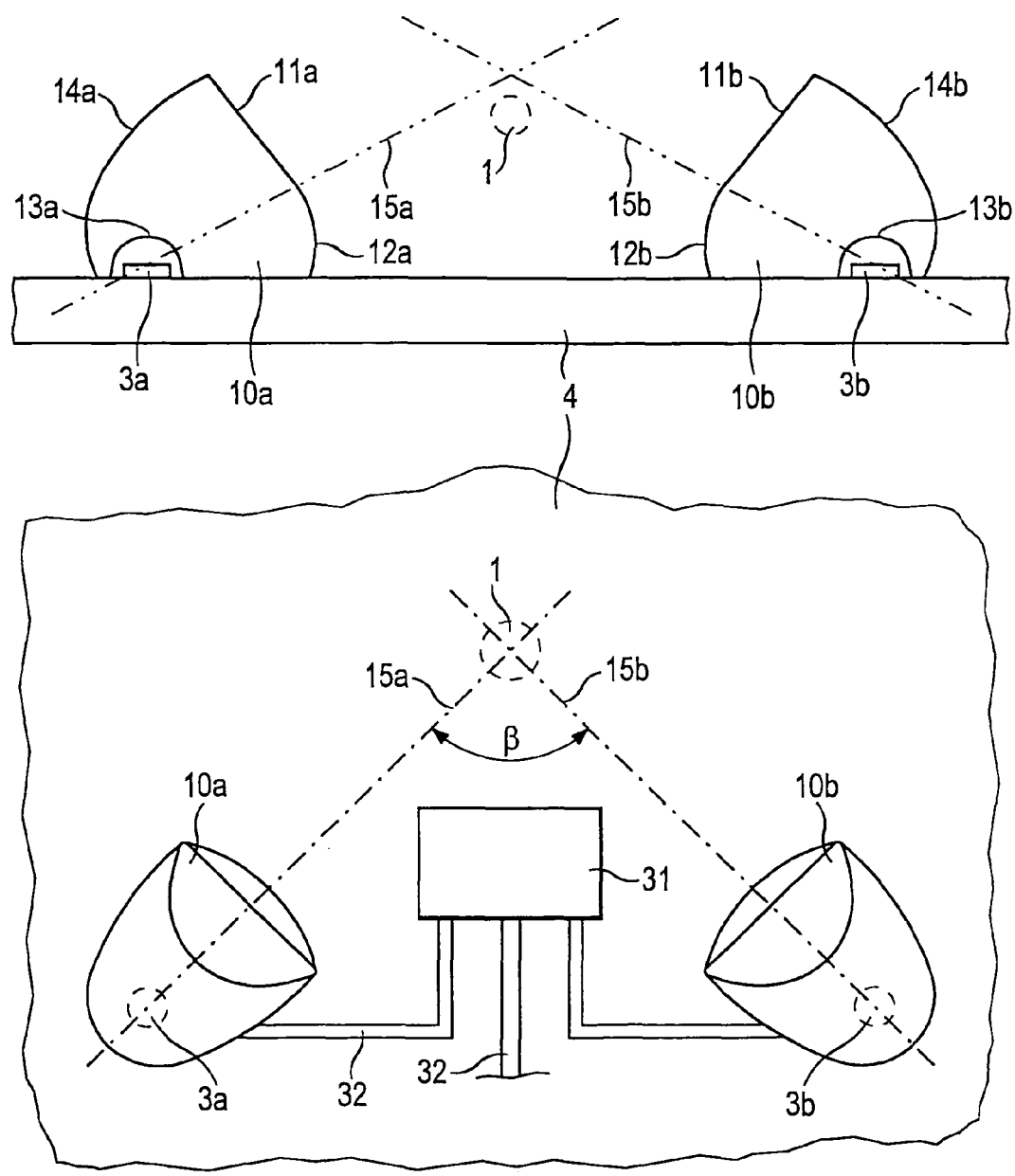
FIG. 3 shows the arrangement of two such radiation guides.

FIG. 3 shows in a side view and in a plain view an arrangement of a scattered light detector, such as a smoke detector. Two radiation guides 10a, 10b are provided. They have the measurement region 1 as common focus. Each of the radiation guides may be formed as described with reference to FIGS. 1 and 2. In the plain view, it shows that the optical axes are not in parallel, but include an angle β smaller than 180°. The arrangement is preferably such that no direct radiation (including reflected radiation) reaches from the radiation source to the radiation sensor.

Radiation guide 10a is allocated to a radiation source 3a, and radiation guide 10b is allocated to a radiation sensor 3b. Radiation sensor 3b is sensitive at least for the radiation, or a part of the radiation, emitted by radiation source 3a. Thus, in radiation guide 10a, radiation is received from radiation source 3a through its third interface 13a and directed towards measurement volume 1 via reflecting surface 14a and first interface 11a, and via second interface 12a. In the measurement volume 1, light scattering takes place in dependence of the presence and quantity of scattering particles, such as smoke particles. Since the measurement volume is the focus region also of the second radiation guide 10b, radiation scattered towards first radiation interface lib and second radiation interface 12b of the second radiation guide 10b will be focused towards sensor 3b and will be sensed there.

The angle β may generally speaking selected such that under optical considerations radiation can reach from source 3a to sensor 3b only through scattering at particles in the ambient fluid, but not directly or through surface reflection. The angle β may be appropriately selected under this provision. It may be a comparative obtuse angle. It may be between 175° and 5°.

31 indicates a circuitry and power supply. It may comprise analogue and/or digital components. 32 symbolizes wiring between circuitry 31 and the electro-optical components and towards external. Depending on the capabilities of circuit 31 the signals towards external may more or less unprocessed sensor signals or may, vice versa, be well prepared and evaluated signals.

Figure 4:
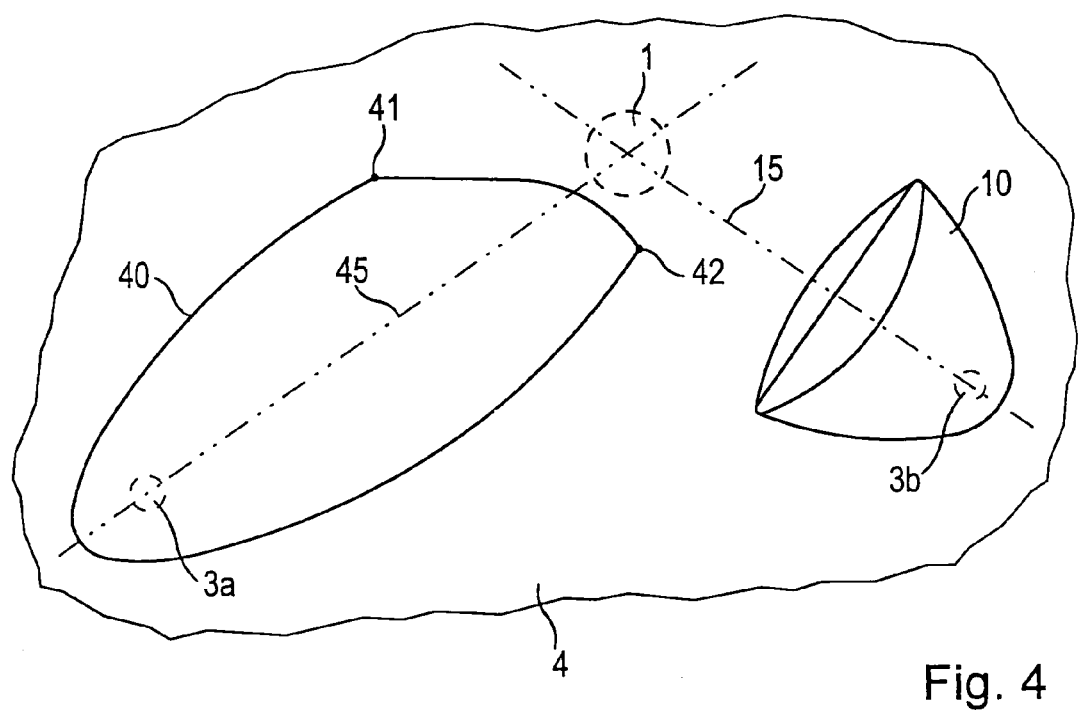
FIG. 4 shows schematically another embodiment of a radiation guide, together with its possible arrangement with another radiation guide.

FIG. 4 shows in combination various other embodiments. It is a plain view similar to that of the lower portion of FIG. 3. Two radiation guides are shown, the right-hand one being formed as described with reference to FIGS. 1 and 2. The left-hand one with reference numeral 40 is formed in another manner: It is a concave shape following a rotation ellipsoid. Such a shape has two focal points. The one of them is again the measurement volume 1. The other of them is to a significant extent surrounded by reflector 40.

The electro-optical component is mounted in this focal point. The reflecting surface is a concave surface of a body with such a formed hollow. The end points or lines 41 and 42 of the rotation ellipsoid reflector towards the measurement volume 1 are selected such that radiation can only through scattering reach from the radiation source 3a to the radiation sensor 3b, and that shading of scattered intensity towards the sensor 3b is avoided.

The body rendering the concave reflective surface may also be surface mountable. Likewise, two bodies may be put together for forming the overall desired shape. The lower half may be a surface portion of the mounting surface itself, onto which a cap-like member for rendering the top portion of the concave reflecting surface is mounted. The radiation guide 40 or the above mentioned cap may in parts also be formed by concave portions in an external cover of the overall sensor.

n the radiation guide 40 of FIG. 4, the focus allocated to the electro-optic component may be surrounded by more than 60% of its circumference by the reflector, whereas the focus at the measurement volume is surrounded by less than 60%.

So far, smoke detector applications were described. But generally speaking, the measurement principle may be used for other detections employing scattering by particles conveyed by or present in a fluid. Further, depending on considerations such as the achievable or necessary intensities, the one or the other of the initially mentioned two measurement principles may be employed, i.e. measuring the scattered intensity, or measuring the weakening of the directly transmitted intensity. In the former case, direct radiation from the radiation source to the radiation sensor must be avoided, as repeatedly mentioned above, whereas in the latter case such a path must be established.

Figure 5:
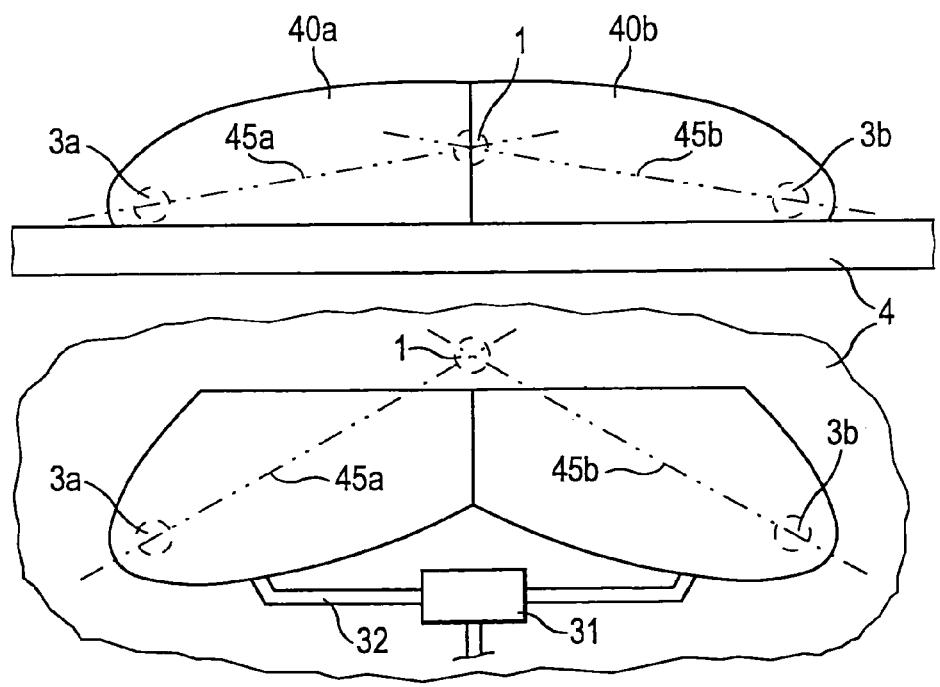
FIG. 5 shows two radiation guides formed as a common body.

FIG. 5 shows an embodiment where both for radiation source 3a and radiation sensor 3b the radiation guide 40a, 40b is formed in accordance with the left-hand side of FIG. 4. In addition to this, the two radiation guides are formed as a joined or common body. 40a denotes the one radiation guide, 40b the other. The one is allocated to a radiation source 3a, the other to a radiation sensor 3b. The measurement volume 1 is at the intersection of the two optical axes 45a, 45b. The reflecting surfaces must again be limited such that in the case of utilizing scattered radiation intensity only such scattered intensity can reach the sensor.

Figure 6:
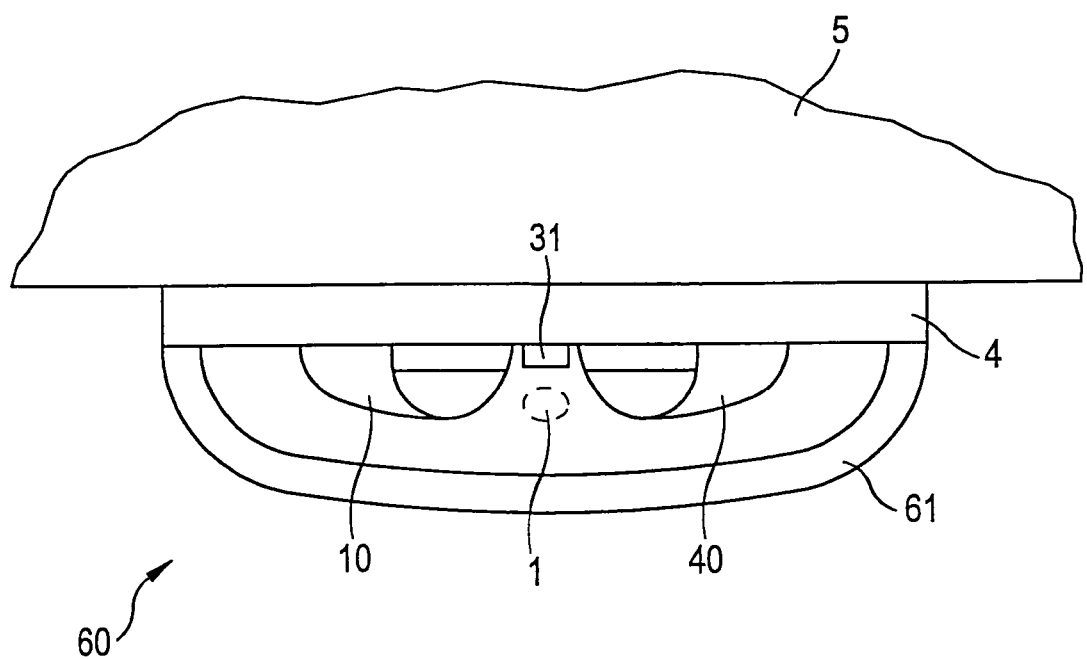
FIG. 6 shows a scattered particle detector.

FIG. 6 shows a scattered intensity detector. It may be a smoke detector mounted at the ceiling 5 of a room to be monitored. 61 is a cover that is fluid permeable and smoke particle permeable, but has light shielding properties as far as required in order to avoid misdetections. 4 is the mounting surface, and schematically shown are two radiation guides 10, 40, arranged in a similar manner as shown in FIG. 3, 4 or 5.

The mounting portions 17a, 17b are formed such that the radiation guide 10 is mounted in a predetermined posture on the mounting surface 4. They may have alignment protrusions for properly placing the radiation guide on the mounting surface. The outside of the radiation guide 10 may be covered by a light shielding substance in order to avoid external radiation entering the radiation guide and thus possibly causing errors. Below the light shielding a reflecting layer may be provided for rendering reflecting surface 14.

The used radiation may be visible radiation or may be infrared radiation. The frequency characteristics of radiation sensor and radiation source match at least in parts. Further, the radiation guide 10 is of a material that is sufficiently transparent for the employed wavelength.

The maximum linear extension of one radiation guide may be 30 mm and preferably 20 mm. The maximum linear extension of an overall detector including its housing may be less than 8 cm, preferably less than 6 cm.

The mounting surface 4 may be any kind of suitable substrate, possibly a printed circuit board on which the electro-optical component 3 is also mounted.

What is claimed is:

1. A surface-mountable radiation guide for a radiation path between a measurement volume and an electro-optical component, comprising:
   a first radiation interface in a radiation path towards the measurement volume;
   a third radiation interface in a radiation path towards the electro-optical component; and
   a reflecting portion forming a first radiation path between the first and the third radiation interface,
   said first radiation path providing a focus region at said measurement volume.

2. The radiation guide according to claim 1 further comprising fixing means for fixing the guide in a predetermined posture on a mounting surface.

3. The radiation guide according to claim 1 wherein the radiation guide comprises a transparent plastic material, and/or a molded or cast body, preferably formed by injection molding, transfer molding, or casting.

4. The radiation guide according to claim 1 wherein the reflecting portion is a part of a surface of a body of the radiation guide which is preferably not coated with a reflecting material.

5. The radiation guide according to claim 1, wherein the radiation guide is cast or molded onto the electro-optical component.

6. The radiation guide according to claim 1 wherein an optical axis of the reflecting portion is tilted compared to the mounting surface.

7. The radiation guide according to claim 1, further comprising:
   a second radiation interface in a radiation path towards the measurement volume,
   wherein radiation travels directly on a second radiation path between the second and the third radiation interface, wherein the second radiation path provides a focus region at said measurement volume.

8. The radiation guide according to claim 7 wherein the first radiation path renders a third focus region close to the third radiation interface.

9. The radiation guide of claim 8, wherein the second radiation path renders a focus region at said third focus region.

10. The radiation guide according to claim 7 wherein the reflecting portion has a cross-sectional shape of at least a part of an ellipse, and the first radiation interface has a straight cross-sectional shape.

11. The radiation guide according to claim 7 wherein the reflecting portion has a cross-sectional shape of at least a part of a parable or following a straight line, and the second radiation interface has a lens cross-sectional shape.

12. The radiation guide according to claim 7 wherein, when seen in a direction perpendicular to the mounting surface, the first and the second radiation interface have portions on different sides of the optical axis.

13. The radiation guide according to claim 7 wherein the first radiation interface is more remote from the mounting surface than the second radiation interface.

14. The radiation guide according to claim 6 wherein the optical axis has a tilt angle against the mounting surface between 0° and 50°.

15. The radiation guide of claim 7 wherein the third radiation interface comprises a concave shaped surface portion for accommodating therein the electro-optical component, particularly a radiation sensor or a radiation source.

16. The radiation guide according to claim 7, wherein the third radiation interface abuts the electro-optical component, particularly a radiation sensor or a radiation source.

17. The radiation guide according to claim 1, wherein the radiation guide is directly or indirectly attached, molded or cast onto an electro-optical element, particularly an emitter or detector, which itself is mounted on a substrate providing electrical terminals that allow connecting an electro-optical component to the outside.

18. A radiation guide for a radiation path between a measurement volume and an electro-optical component comprising a first radiation path between a first and a third radiation interface, and a second radiation path between a second and said third radiation interface, wherein:
   the first radiation path has a reflecting portion between the first and the third radiation interface;
   the second radiation path has no reflecting portion between the first and the third radiation interface; and
   both the first and second radiation paths are formed to render focus regions on both sides thereof outside the radiation guide,
   wherein the corresponding focus regions of the first and the second radiation path coincide.

19. The radiation guide according to claim 18, wherein the radiation guide is configured:
   for guiding light radiation, preferably in the visible wavelength range (400 nm-800 nm) and/or in the IR range with wavelengths preferably up to 1200 nm and possibly larger;
   its maximum linear extension is less than 50, preferably 30 mm;
   it is customized for a scattered radiation detector, particularly for a smoke detector;
   one or more of the first, second and third radiation interfaces are a surface portion of the body of the radiation guide;
   the reflecting portion is at least partially a part of a shape having rotation-symmetry around an optical axis; and
   a mounting surface is a printed circuit board.

20. A radiation guide for a radiation path between a measurement volume and an electro-optical component, comprising:
   a first reflector having a concave reflecting surface being a part of a rotational ellipsoid, the first reflector configured for mounting in relation to the electro-optical component such that a first focus region of the reflecting surface of the first reflector is at the electro-optical component.

21. The radiation guide according to claim 20, wherein in a cross-section through an optical axis of the first reflector said first focus region is surrounded by more than 60% of its circumference by said reflector and a second focus region is surrounded by less than 60%.

22. The radiation guide according to claim 20, further comprising a mounting portion for mounting the radiation guide on a mounting surface.

23. The radiation guide according to claim 20 further comprising a second reflector having a second concave reflecting surface being a part of a rotational ellipsoid, the second reflector configured to be mounted in relation to a second electro-optical component such that a further focus region of the second reflecting surface is at a second electro-optical component, wherein the first and the second reflector are formed as one part.

24. The detector according to claim 23, wherein the radiation guide allocated to the radiation sensor is configured such that its optical interface towards the measurement volume is not located in an aperture angle at said measurement volume rendered by the radiation guide allocated to the radiation source.

25. A scattered radiation detector, preferably a smoke detector, comprising:
a radiation source;
a measurement volume accessible for a fluid capable of carrying a scattering substance;
a radiation sensor;
a radiation guide comprising a concave reflecting surface being a part of a rotational ellipsoid between the measurement volume and at least one of radiation source and radiation sensor; and
a housing accommodating the radiation source, the measurement volume, the radiation sensor, and the radiation guide.

26. The detector according to claim 25, further comprising a first radiation guide between the measurement volume and the radiation source and a second radiation guide between the measurement volume and the radiation sensor.

27. The detector according to claim 25, further comprising an auxiliary radiation guide between an electro-optical component and the radiation guide.

28. The detector according to claim 27, further comprising a circuit board on which the electro-optical component and the radiation guide are mounted.

29. The detector according to claim 25, wherein the radiation guide or a part thereof is formed as a part of and preferable integrally with, a part of the housing.

30. A scattered radiation detector, preferably a smoke detector, comprising:
a radiation source;
a measurement volume accessible for a fluid capable of carrying a scattering substance;
a radiation sensor;
a first radiation guide between the measurement volume and the radiation source;
a second radiation guide between the measurement volume and the radiation sensor; and
a housing accommodating the radiation source, the measurement volume, the radiation sensor, and the radiation guide,
wherein the first radiation guide and the second radiation guide each comprise a first radiation interface in a radiation path towards the measurement volume, a third radiation interface in a radiation path towards an electro-optical component, a reflecting portion forming a first radiation path between the first and the third radiation interface, said first radiation path providing a focus region at said measurement volume.

31. A scattered radiation detector, preferably a smoke detector, comprising:
a radiation source;
a measurement volume accessible for a fluid capable of carrying a scattering substance;
a radiation sensor;
a first radiation guide between the measurement volume and the radiation source;
a second radiation guide between the measurement volume and the radiation sensor; and
a housing accommodating the radiation source, the measurement volume, the radiation sensor, and the radiation guide,
wherein one of the first and second radiation guides comprises a first radiation interface in a radiation path towards the measurement volume, a third radiation interface in a radiation path towards an electro-optical component, a reflecting portion forming a first radiation path between the first and the third radiation interface, said first radiation path providing a focus region at said measurement volume, and an other of the first and second radiation guide comprises a first reflector having a concave reflecting surface being a part of a rotational ellipsoid, the first reflector configured for mounting in relation to an electro-optical component such that a first focus region of the reflecting surface of the first reflector is at the electro-optical component.

32. , A scattered radiation detector, preferably a smoke detector, comprising:
a radiation source;
a measurement volume accessible for a fluid capable of carrying a scattering substance;
a radiation sensor;
a first radiation guide between the measurement volume and the radiation source;
a second radiation guide between the measurement volume and the radiation sensor; and
a housing accommodating the radiation source, the measurement volume, the radiation sensor, and the radiation guide,
wherein each of the first and second radiation guides comprises a first reflector having a concave reflecting surface being a part of a rotational ellipsoid, the first reflector configured for mounting in relation to an electro-optical component such that a first focus region of the reflecting surface of the first reflector is at the electro-optical component.

33. A substrate comprising an arrangement portion for an electro-optical component and alignment means for a mold for a radiation guide for a radiation path between a measurement volume and the electro-optical component, the radiation guide comprising:
a first radiation interface in a radiation path towards the measurement volume;
a third radiation interface in a radiation path towards the electro-optical component; and
a reflecting portion forming a first radiation path between the first and the third radiation interface, said first radiation path providing a focus region at said measurement volume.

34. A substrate comprising an arrangement portion for an electro-optical component and an arrangement portion for a radiation guide for a radiation path between a measurement volume and the electro-optical component, the radiation guide comprising:
a first radiation interface in a radiation path towards the measurement volume;

a third radiation interface in a radiation path towards the electro-optical component; and a reflecting portion forming a first radiation path between the first and the third radiation interface, said first radiation path providing a focus region at said measurement volume, wherein, the arrangement portion includes alignment means for said radiation guide.

35. A smoke detector component comprising a radiation guide and an electro-optical element, the radiation guide for a radiation path between a measurement volume and the electro-optical component, the radiation guide comprising:

a first radiation interface in a radiation path towards the measurement volume; a third radiation interface in a radiation path towards the electro-optical component; and a reflecting portion forming a first radiation path between the first and the third radiation interface, said first radiation path providing a focus region at said measurement volume.

36. The component of claim 35, further comprising a substrate.

* * * * *